(12) United States Patent
Ma et al.

(10) Patent No.: US 8,519,192 B2
(45) Date of Patent: Aug. 27, 2013

(54) PROCESS FOR PRODUCING 2-(CYCLOHEX-1'-ENYL)CYCLOHEXANONE

(75) Inventors: Ying-Ling Ma, Kaohsiung (TW); Chia-Hui Shen, Tainan (TW); Chien-Chu Chen, Kaohsiung (TW)

(73) Assignee: China Petrochemical Development Corporation (TW)

( * ) Notice: Subject to any disclaimer, the term of this patent is extended or adjusted under 35 U.S.C. 154(b) by 35 days.

(21) Appl. No.: 13/297,687

(22) Filed: Nov. 16, 2011

(65) Prior Publication Data
US 2012/0059193 A1 Mar. 8, 2012

(30) Foreign Application Priority Data
Dec. 28, 2010 (TW) ................. 99146246 A

(51) Int. Cl.
*C07C 45/45* (2006.01)
(52) U.S. Cl.
USPC .......................... 568/338; 568/353

(58) Field of Classification Search
USPC ................................. 568/338, 353
See application file for complete search history.

(56) References Cited

U.S. PATENT DOCUMENTS

| 3,880,930 A | 4/1975 | Ramm et al. |
| 3,980,716 A | 9/1976 | Elliott |
| 4,002,693 A | 1/1977 | King et al. |

FOREIGN PATENT DOCUMENTS

CN 101205170 6/2008

OTHER PUBLICATIONS

Yuelan, Feng, et al., "Synthesis of 0-Phenylphenol from Cyclohexanone in One Stage", Fine Chemicals, 11 (5), pp. 42-45 (1994) (with English Abstract).

*Primary Examiner* — Sikarl Witherspoon
(74) *Attorney, Agent, or Firm* — Harness, Dickey & Pierce, P.L.C.

(57) ABSTRACT

The present invention discloses a process for producing 2-(cyclohex-1'-enyl)cyclohexanone by an auto-condensation of cyclohexanone at a certain temperature in the presence of a certain solid acidic catalyst.

5 Claims, No Drawings

PROCESS FOR PRODUCING 2-(CYCLOHEX-1'-ENYL)CYCLOHEXANONE

FIELD OF THE INVENTION

The present invention relates to a process for producing 2-(cyclohex-1'-enyl)cyclohexanone by an auto-condensation of cyclohexanone at a certain temperature in the presence of a certain solid acidic catalyst.

BACKGROUND TO THE INVENTION 2-(cyclohex-1'-enyl)cyclohexanone is an important, widely used chemical product. In addition to being used as a modifying agent for epoxy resins, a plasticizer, and a crosslinking agent for polymers, it is also an intermediate in the synthesis of o-phenylphenol, which is an important fine organic chemical. O-phenylphenol can be widely used in synthesizing dyes, surfactants, fire retardants, plastic stabilizing agents, pharmaceuticals, etc., and its market demand also increases continuously as its uses are developed unceasingly.

O-phenylphenol can be produced: 1. by dehydro-condensation of cyclohexanone, 2. by sulfonation- or halogenation-hydrolysis of phenylbenzene, 3. by diazotization-hydrolysis of aminophenylbenzene, 4. by hydrolysis of chlorobenzene under high pressure, 5. from dibenzofuran, or 6. by coupling of chlorobenzene and phenol. Among the aforementioned synthesis processes, the most widely used process is currently the process of dehydro-condensation of cyclohexanone. The process of dehydro-condensation of cyclohexanone can be divided into two stages; the first stage is condensing cyclohexanone in the presence of an acidic or basic catalyst to obtain a dimer of 2-(cyclohex-1'-enyl)cyclohexanone, and the second stage is dehydrogenating 2-(cyclohex-1'-enyl)cyclohexanone with a catalyst containing a metal such as Pt to produce o-phenylphenol.

As stated above, 2-(cyclohex-1'-enyl)cyclohexanone is produced from the acid- or base-catalyzed condensation occurring between cyclohexanone molecules, and its reaction equation is shown as below:

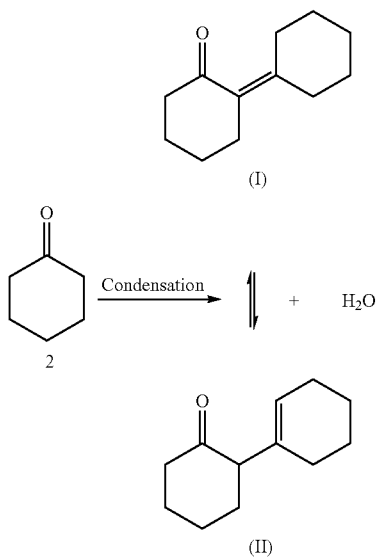

Generally, the auto-condensation of cyclohexanone will produce two kinds of resonance isomers (I) and (II), of which 2-(cyclohex-1'-enyl)cyclohexanone (II) is usually predominant. Both the two kinds of compounds can proceed to the subsequent dehydrogenation reaction to prepare o-phenylphenol.

Currently, the published patents relating to catalysts for use in the auto-condensation of cyclohexanone to produce 2-(cyclohex-1'-enyl)cyclohexanone can be roughly classified into four kinds, including inorganic strong acids/bases, organic acids, organic metal compounds, and solid acidic catalysts.

In U.S. Pat. No. 4,002,693, sulfuric acid is used as the catalyst, and the yield of 2-(cyclohex-1'-enyl)cyclohexanone is about 37%. However, the use of sulfuric acid as the catalyst has many disadvantages. First, the investment in the reactor equipment is higher due to the strong corrosive property of sulfuric acid. Second, if concentrated sulfuric acid is used as the catalyst, its strong oxidation property and strong dehydration property will cause increased reaction by-products; on the other hand, the use of diluted sulfuric acid may reduce the occurrence of side reactions, but will cause excessive water to remain in the reaction system, which will lower the convertibility of the reaction. Third, the catalyst of sulfuric acid cannot be reused, the cost of the process is high, and the waste water from the process causes environmental problems.

U.S. Pat. No. 3,980,716 discloses that a compound formed of aliphatic carboxylic acid, naphthenic acid, heteropolyacid, ethylenediamine tetra-acetic acid and acetylacetonate with a metal such as Ti, V, Cr, Mn, Fe, Co, Ni, Cu, Zn, Zr, Mo, Cd, Sn and W, or their alkoxides can be used as the catalyst in the auto-condensation of cyclohexanone to produce dimers, in which vanadium stearate as the catalyst has a better performance, and the conversion of cyclohexanone and the selectivity of dimer are 71% and 89%, respectively. However, the reaction must be carried out in the absence of air, and the high conversion needs the reaction temperature to be as high as 190° C.

In U.S. Pat. No. 3,880,930, a sulfonic acid type cation exchange resin, benzene sulfonic acid or toluene sulfonic acid are used to catalyze the auto-condensation of cyclohexanone to produce dimers. The highest conversion is 59.9%, and the selectivity is 90%. However, the biggest disadvantage of an acidic resin is its poor heat resistance, and therefore the reaction must be carried out at a reduced pressure to lower the reaction temperature; otherwise, the catalyst tends to be deactivated, and the investment in equipment and the energy consumption are high. In addition, benzene sulfonic acid and toluene sulfonic acid are also strong organic acids, and therefore have the same disadvantages as sulfuric acid, which tends to corrode the equipment.

The research made by Institute of Coal Chemistry, Chinese Academy of Sciences, shows that the conversion of cyclohexanone is 52.4% and the selectivity of dimer is 99.2% when the dimerization of cyclohexanone is carried out in a packed bed reactor at 350° C. in the presence of 5% of $NaNO_2$-rare earth element/$\gamma$-$Al_2O_3$ catalyst. However, the conversion is low, the reaction temperature is too high and the energy consumption is large, which make the process have no superiority [Fine Chemicals, 1994, 11(5), 42-45].

China Pat. No. 101 205 170 proposes an improved catalyst. The auto-condensation of cyclohexanone is carried out in a batch reactor with an $Al_2O_3$ catalyst obtained by calcination of a pseudo-boehmite precursor, and the yield can be 70% or above.

SUMMARY OF THE INVENTION

In view of the aforementioned disadvantages that exist in the processes of self-condensation of cyclohexanone to produce dimers, it is an object of the present invention to provide a process for producing 2-(cyclohex-1'-enyl)cyclohexanone, by which 2-(cyclohex-1'-enyl)cyclohexanone can be produced from an auto-condensation of cyclohexanone under a relatively mild reaction condition.

Another object of the present invention is to provide a process for producing 2-(cyclohex-1'-enyl)cyclohexanone that can improve the yield of 2-(cyclohex-1'-enyl)cyclohexanone.

Yet another object of the present invention is to provide a process for producing 2-(cyclohex-1'-enyl)cyclohexanone that can reduce the corrosion of production equipment.

According to the present invention, a novel solid acidic catalyst is used to catalyze the auto-condensation of cyclohexanone so as to produce 2-(cyclohex-1'-enyl)cyclohexanone from cyclohexanone. The solid acidic catalyst is represented by the following empirical formula:

$$Al_xS_yO_z$$

wherein x, y and z represent an atomic ratio, and x is 1 to 4, y is 1 to 3, and z is a number taken to satisfy the valence requirements of Al and S in the oxidation states in which they exist in the catalyst.

According to a preferred embodiment of the present invention, the solid acidic catalyst can be prepared by soaking $Al(OH)_3$ in a 0.5-2.5 M sulfuric acid solution for 1 hour, which is then calcined at 450° C. or above after being dried. In addition, the solid acidic catalyst is added at an amount of 2% by weight or above, based on the total weight of the reaction solution; the reaction is carried out at a temperature of from 100 to 160° C., and preferably from 130 to 150° C.

The present invention can be applied to a batch process and a continuous process, including continuous stirred tank reactor (CSTR), packed bed reactor, fluidized bed reactor, etc.

The features and effects of the present invention will be further explained with reference to the preferred embodiments below, which are, however, not intended to restrict the scope of the present invention.

DESCRIPTION OF PREFERRED EMBODIMENTS

The conversion of cyclohexanone and the selectivity of dimer are calculated according to the following equations:

Conversion(%)={[Concentration of added cyclohexanone−Concentration of unreacted cyclohexanone](mol)/Concentration of added cyclohexanone(mol)}×100%

Selectivity(%)={2×Concentration of product dimer (mol)/[Concentration of added cyclohexanone−Concentration of unreacted cyclohexanone](mol)}×100%

Examples 1-3

(1) Preparation of Catalyst $Al(OH)_3$ soaked in a 0.6 M sulfuric acid solution was placed at room temperature for 1 hour, and then filtered. After drying and then calcination at 450° C. or above, an experimental catalyst was obtained.

(2) Test of Condensation Reaction 568.2 g of cyclohexanone and 23.7 g of the catalyst made above were placed in a 1-L stainless steel reactor equipped with a mechanical stirrer. The reaction temperatures were controlled at 130° C., 140° C. and 150° C., respectively. During the reaction, the reactant cyclohexanone itself functioned as a water-carrying agent, and additional nitrogen was introduced to assist in removing the water produced by the reaction. Samplings were conducted at 2 hours, 4 hours and hours, and the samples were analyzed with a gas chromatographer and a moisture titrator. The results are listed in Table 1.

TABLE 1

Influence of Temperature on Production of 2-(cyclohex-1'-enyl)cyclohexanone

| No. | Temp. | 2 hours Conversion (%) | 2 hours Selectivity (%) | 4 hours Conversion (%) | 4 hours Selectivity (%) | 6 hours Conversion (%) | 6 hours Selectivity (%) |
|---|---|---|---|---|---|---|---|
| Ex1 | 130° C. | 13.8 | 100.0 | 26.5 | 100.0 | 37.9 | 100.0 |
| Ex2 | 140° C. | 38.3 | 92.5 | 72.5 | 95.5 | 86.3 | 92.0 |
| Ex3 | 150° C. | 68.4 | 93.8 | 89.9 | 86.4 | 95.1 | 83.3 |

From the experimental results shown in Table 1, it can be found that the catalyst according to the present invention can effectively promote the auto-condensation of cyclohexanone, and the reaction rate and yield increase as the increase of reaction temperature.

Examples 4-6

(1) Preparation of Catalyst

The experimental catalyst was prepared by the same method as shown in Examples 1-3.

(2) Test of Condensation Reaction 568.2 g of cyclohexanone, and 49.41 g, 77.48 g and 108.23 g, respectively, of the catalyst made above were placed in a 1-L stainless steel reactor equipped with a mechanical stirrer. The reaction temperatures were controlled at 140° C. During the reaction, the reactant cyclohexanone itself functioned as a water-carrying agent, and additional nitrogen was introduced to assist in removing the water produced by the reaction. Samplings were conducted at 2 hours, 4 hours and hours, and the samples were analyzed with a gas chromatographer and a moisture titrator. The results are listed in Table 2.

TABLE 2

| | | 2 hours | | 4 hours | | 6 hours | |
|---|---|---|---|---|---|---|---|
| No. | Amt. of Catalyst | Conversion (%) | Selectivity (%) | Conversion (%) | Selectivity (%) | Conversion (%) | Selectivity (%) |
| Ex2 | 4 wt. % | 38.3 | 92.5 | 72.5 | 95.5 | 86.3 | 92.0 |
| Ex4 | 8 wt. % | 65.4 | 93.5 | 86.1 | 87.3 | 89.3 | 79.9 |
| Ex5 | 12 wt. % | 78.1 | 93.6 | 90.0 | 75.7 | 95.7 | 66.0 |
| Ex6 | 16 wt. % | 82.7 | 85.8 | 91.8 | 67.4 | 95.3 | 52.6 |

Influence of Catalyst Concentration on Production of 2-(cyclohex-1'-enyl)cyclohexanone From the experimental results shown in Table 2, it can be found that increasing the amount of catalyst can effectively enhance the reaction rate, and can shorten the reaction time in the maintenance of 70% or above yield.

The entire disclosure of Taiwan Patent Application No. 099146246 filed on Dec. 28, 2010 is incorporated by reference.

What is claimed is:

1. A process for producing 2-(cyclohex-1'-enyl)cyclohexanone by an auto-condensation of cyclohexanone at a certain temperature in the presence of a solid acidic catalyst, wherein the solid acidic catalyst is represented by the following empirical formula:

$$Al_xS_yO_z$$

wherein x, y and z represent an atomic ratio, and x is 1 to 4, y is 1 to 3, and z is a number that satisfies the valence requirements of Al and S in the oxidation states in which they exist in the catalyst.

2. The process according to claim 1, wherein x is 1 to 2, and y is 1 to 2.

3. The process according to claim 1, wherein the solid acidic catalyst is present at an amount of 2% by weight or above, based on the total weight of the reaction solution.

4. The process according to claim 1, wherein the reaction is carried out at a temperature of from 100 to 160° C.

5. The process according to claim 4, wherein the reaction is carried out at a temperature of from 130 to 150° C.

* * * * *